(12) United States Patent
Fliedner (10) Patent No.: US 8,523,935 B2
(45) Date of Patent: Sep. 3, 2013

(54) TUBULAR SUPPORT PROSTHESIS WITH LATERALLY OVERLAPPING ARCS OF CURVATURE

(75) Inventor: Thilo Fliedner, München (DE)

(73) Assignee: Axetis AG C/O Zulauf Asset Management AG, Zug (CH)

( * ) Notice: Subject to any disclaimer, the term of this patent is extended or adjusted under 35 U.S.C. 154(b) by 1200 days.

(21) Appl. No.: 11/502,037

(22) Filed: Aug. 10, 2006

(65) Prior Publication Data
US 2007/0055353 A1    Mar. 8, 2007

(30) Foreign Application Priority Data

Aug. 10, 2005  (EP) .................................. 05017419

(51) Int. Cl.
    *A61F 2/06*    (2006.01)
(52) U.S. Cl.
    USPC ....................................................... 623/1.16
(58) Field of Classification Search
    USPC .............................. 623/1.15, 1.16
    See application file for complete search history.

(56) References Cited

U.S. PATENT DOCUMENTS

| 6,620,201 | B1 | 9/2003 | Nadal et al. |
| 2003/0105515 | A1* | 6/2003 | Skubitz et al. ............... 623/1.15 |
| 2003/0144729 | A1 | 7/2003 | Bicek et al. |
| 2004/0102831 | A1 | 5/2004 | Murray, III |
| 2004/0127972 | A1 | 7/2004 | Kitaoka et al. |
| 2005/0043778 | A1 | 2/2005 | Von Oepen et al. |

FOREIGN PATENT DOCUMENTS

| DE | 101 23 441 A | 3/2001 |
| EP | 0 790 041 A | 8/1997 |

OTHER PUBLICATIONS

Search Report of EP 36482 MATL dated Dec. 28, 2005.

\* cited by examiner

*Primary Examiner* — S. Thomas Hughes
*Assistant Examiner* — Julie A Szpira
(74) *Attorney, Agent, or Firm* — Sughrue Mion, PLLC (57) ABSTRACT

The present invention refers to a tubular support prostheses (stent) for vessels or intercorporeal lumina comprising at least two adjacently arranged expandable support rings connected to one another on at least one joint, said support rings being formed by a filament wound in a meander-like manner to form several arcs of curvature. The expansion behavior of such a support prosthesis is to be improved. For this purpose at least one arc of curvature of a first support ring and an arc of curvature of an adjacent second support ring overlap laterally, whereby the joint in the overlapping portion is formed.

16 Claims, 7 Drawing Sheets

TUBULAR SUPPORT PROSTHESIS WITH LATERALLY OVERLAPPING ARCS OF CURVATURE

The present invention refers to a tubular support prosthesis, particular a vessel stent, for vessels or intracorporeal lumina, comprising at least two adjacently arranged, expandable support rings, which are connected to one another at least at one joint, each being formed by a filament wound in a meander-like manner, to form several arcs of curvature.

One such support prosthesis is e.g. known from DE 295 21 206 U1. The "stent" described there comprises several adjacently arranged support rings, each consisting of a regular filament shaped in a meander pattern. Some of the arcs of curvature or loops of the meander pattern of a support ring are connected with associated arcs of curvature of an adjoining support ring via connectors which are also loop-shaped. Due to the loop shape of the connectors, these connectors elongate when expanding the vessel stent so that longitudinal shrinking produced by expanding the support ring is compensated for and the vessel stent substantially maintains its original length. The meander shape and the shape and arrangement of the connectors are chosen such that the individual arcs of curvature or loops do not flare when expanding the vessel stent, which could lead to an unnecessary damage of the vessel wall. The vessel stents are usually brought to the target location by means of a catheter, where they are expanded by means of a balloon (balloon catheter) in the vessel by expansion of the support rings connected to one another to the required lumen and the required diameter for supporting the vessel.

However, it is difficult with known stents to simultaneously fulfil the different demands by a suitable forming of the support rings and connectors. Measures, effecting a minimal longitudinal shrinking during expansion do not always lead to a desired stability against erection of the arcs of curvature of the meander shape. Moreover, vessel stents are often provided with coatings to improve compatibility. Such coatings must sometimes be capable of withstanding extreme deformations when expanding the vessel stent.

It is now the object of the invention to provide a support prosthesis of the above-mentioned kind, with improved properties with respect to a reduced erection tendency of the arcs of curvature while preferably avoiding stress peaks to a great extent.

This object is solved according to the invention with a tubular support prosthesis of the above-mentioned kind in that at least one arc of curvature of a first support ring and one arc of curvature of an adjacent second support ring laterally overlap and that the joint is formed in the overlapping portion.

So far the support rings have always been arranged side by side and contacted each other, if at all, in the area of some apexes of curvature to produce a connection. Most of the time they are spaced apart and are connected to one another by specially shaped connectors. The overlapping refers according to the invention to the shortest distance of two circumferential centerlines to the adjoining support ring. The overall width of a support ring (measured perpendicular with respect to this centerline) must therefore be larger than the distance of both of these mentioned centerlines. By this definition, an apparent overlapping in obliquely arranged or elliptical support rings is to be excluded. The overlapping ensures that the adjoining support rings are virtually interlocked and the arcs of curvature at the joints in the curvature portion mutually prevent each other from flaring of the arcs of curvature during the expansion process. Moreover, stress peaks in the joint can be reduced by such a measure as compared to conventional vessel stents, so that this structure is also well suited for coatings. The vessel stents are preferably made of a tubular blank in which the meander-like shaped support rings or the filamant forming the same are lasered out of the full material and is/are subsequently electro-polished. By such a manufacturing method, extremely filigree, network-like structures may be generated.

Overlapping arcs of curvature may preferably have a common filament section in the overlapping portion, said filament section forming the joint. The connector is therefore part of the arcs of curvature theselves at a position at which these overlapping arcs of curvature contact each other or merge into each other. The overlapping portion then has a direct influence on the deformation of the arcs of curvature themselves when expanding the vessel stent. Formerly used connectors are intended to develop their own deformation properties as independently as possible from the arcs of curvature and only served for fixing two adjoining arcs of curvature apex points with respect to one another. The design variant according to the invention allows the generation of, a far more complex deformation process which, however, finally leads to an improvement of the expansion behavior of the vessel stent.

One embodiment provides that a circumferential annular centerline of a support ring is arranged essentially in a cross-sectional plane extending perpendicular with respect to the main axis of the support prosthesis. The circumferential annular centerline is arranged centrally between the two front ends of a support ring, so that at least the apices of the arcs of curvature overlapping with other arcs of curvature of adjoining support rings are equally spaced to this centerline. If this centerline is arranged in a cross-sectional plane extending perpendicular with respect to the support prosthesis main axis, the support rings extend circularly or straightly and not obliquely or elliptically around the support prosthesis main axis. This avoids additional power components, which would occur in an oblique arrangement of the support rings.

Moreover, the meander shape of the filament of a support ring may have at least two different arcs of curvature shapes or sizes, which together form a recurring pattern of the meander shape. One could also speak of a periodically circumferential pattern sequence. While in the common vessel stents regular meander patterns are used, an irregular pattern is used in the vessel stent according to the invention due to different arcs of curvature shapes, so that the period is larger. This allows the deformation behavior during expansion within a certain range to be influenced to a greater degree. Particularly if tighter and wider arcs of curvature and longer or shorter arcs of curvature are used, a targeted step-wise expansion of the vessel stent can be carried out.

Moreover, a prosthesis window advantageously formed between two overlapping portions connected to one another may have a first frame half formed by the first support ring, and a second frame half formed by the adjacent second support ring, wherein both frame halves are formed centrically with respect to one another. If an irregular meander shape is chosen, a centricality of the window frame half leads to the same expansion properties, however in the opposite direction, which leads to a regularity in the expansion properties.

In order to achieve that the joints possibly counteract a shrinking of the length of the vessel stent during the expansion process, it is provided in an embodiment that the common filament section in the overlapping portion is included at an angle $\alpha$ of larger than 0°, preferably larger than 10°, relative to a parallel of the support prosthesis main axis. The inclination ensures that the joint pivots when expanding the vessel stent, in particular that it moves towards an angle in the range of 90°. This counteracts a length reduction.

In this connection, an embodiment turned out to be advantageous with respect to a reduced change in length, in which the angle α at at least one overlapping portion is 15°-25° and at the other overlapping portions it is 165° to 155°. Both angles are measured from the same reference line, which is why it can be referred to an opposite inclination of the overlapping portions so that partially the overlapping portions during expansion erect in a clockwise direction and partially in a counterclockwise direction, which in turn leads to a regularity of the expansion.

The common filament sections of the overlapping portions between two adjoining support rings are preferably all inclined in the same direction. Caused by these constructive measures, the length change ratios are equally large on one side of a support ring caused by the erection of the overlapping portions during the expansion process. According to a further embodiment, it can also be provided that the common filament sections of the overlapping portions are inclined on the one side of a support ring in the opposite direction with respect to the overlapping portions of the other side of the same support ring. The overlapping portions on the opposite side of a support ring virtually pivot towards each other during the expansion process so that part of the expansion fluctuations is reduced again.

A regularity of the stress situation can particularly be achieved in a variant in that a support ring is connected circumferentially alternately on the one side with an adjoining support ring and on the other side with a further adjoining support ring. Thus, a support ring is connected between two overlapping portions arranged behind one another in the circumferential direction on the one side with a further support ring. The joints or overlapping portions therefore change the side along the circumference of a support ring in a zigzag manner.

The interlocking of the support rings may favorably be selected such that the ratio of the length of the overlapping portion, seen in the longitudinal direction of the support prosthesis, to the width of the support ring is larger than 0.1, preferably larger than 0.2. By this is it usually ensured that not only the apex portions of the arcs of curvature overlap each other, but also that parts of the legs of the arcs of curvature contribute to forming the overlapping portion. This design has a positive influence on the deformation behavior and particularly counteracts an erection of the arcs of curvature during the expansion process.

Moreover, each arc of curvature may comprise a first leg, a second leg and an apex section extending between these legs, wherein the first and the second leg are curved in the same direction. Such an additional curvature, so that the arcs of curvature have the contour of a fin or claw, has been unusual up to now. This constructional measure mainly serves for a regularity of the expansion behavior of the vessel stent. An additional design provides that the first and second legs of the arcs of curvature of a support ring are curved in the same direction and the first and second legs of the arcs of curvature of the adjoining support rings are curved in the opposite direction. This again leads to a regularity of the expansion behavior, since the effect achieved by this form develops in both directions. Moreover, this measure leads to the fact that a possibly long overlapping portion can be formed without the space requirement becoming too large.

By means of a further embodiment, a coating may be provided on the filament, said coating comprising silicon dioxide. Thus, a glass-like coating may be provided. The silicon dioxide may exist in amorphous or in crystalline or semi-crystalline form.

The properties of the coating may furthermore be modified by at least one admixture, which is contained in the coating, wherein the admixture may be selected from among aluminum oxide, titanium oxide, calcium compounds, sodium oxide, ground oxide, magnesium oxide, selenium oxide and hydroxides, particularly hydroxides of the above-mentioned metals. Especially preferred admixtures are aluminum oxide and titanium oxide.

If an admixture of silicon dioxide is used, the proportion of the admixture to the overall amount of the coating may preferably be 0.5 to 50 percent by weight.

In order to maintain the desired surface properties over the entire surface of the support prosthesis, it is preferred that the coating is substantially pore-free.

However, it may also be preferred in certain embodiments that the coating comprises pores for a functionalization with further substances which are applied onto the coating after the actual coating and which deposit in the pores. Accordingly, the coating may comprise an additional or only a partial or punctually existing functionalization coating. Such a coating may correspond to the medical purpose of the support prosthesis and include the influence of growth of surrounding tissue, a killing of undesired tissue, the generation of a relation between the support prosthesis and the tissue etc. The functionalization coating may comprise for instance at least a medicament and/or at least a cellular toxin.

A great advantage of the support prosthesis according to the invention is to be seen in that the coating can be applied extremely thinly, namely preferably in the nanometer range, i.e. in the range of some layers of atoms, which allows during the manufacture of the support prostheses to be able to substantially set the final dimensions without having to take dimensional changes by the coating into consideration that are possibly not exactly predictable. The thickness of the coating according to the invention is preferably 0.1 to 1000 nm. However, it is self-evident that both thinner as well as thicker coatings are possible. The decisive factor for the selection of the layer thickness is the demand that in the case of expansion of the support prosthesis in the body the coating is not damaged and no additional pores are produced.

The coating may be applied in a single step, and thus form a single-layered layer, however, in a preferred embodiment it may also consist of several successively applied layers. In the case of a multi-layered application, the composition of each individual step can be defined individually. The support prosthesis comprises a carrier forming the basic structure, which is at least partially provided with the coating.

The carrier is preferably made of a persistent material, wherein "persistent" is a property in which the material after implantation into a body does not show any degradation at least for one year.

The carrier of the support prosthesis may comprise conventional materials, such as carbon, PTFE, Dacron, metal alloys or PHA, wherein particularly steel alloys are preferred materials.

The metal alloys used for the carrier are preferably selected from the group of stainless steels.

A further preferred material for the carrier is a shape memory metal, particularly nickel-titanium alloy, which is used in such support prostheses due to its ability to independently change shape.

A method of producing the support prostheses may comprise the following steps:
  providing a carrier forming the basic structure; and
  applying a silicon dioxide-containing coating by means of
    a plasma coating method.

In order to obtain the pores for receiving functionalization means desired in certain embodiments, it is also preferred that the method comprises a step of generating pores in the coating by means of a neutron bombardment. For this purpose, neutron sources such as particle accelerators can be used. A further variant for generating function pores is to manufacture the pores by means of laser light.

The above-described coating substantially prevents, due to its inert, glass-like surface with silicon dioxide, a covering by cells of the body or an adherence of such cells, since due to its hardness it counteracts damage during introduction of the support prosthesis into the body and thus facilitates handling, which caused by the thinness of the coating allows a simple design of the support prosthesis. Moreover, it has a reduced friction caused by the lower roughness values, and thus a smaller load for blood components and lower coagel formation, wherein even after a longer dwelling time any degradation of the coating does not occur.

In a further embodiment it is provided that each arc of curvature has a portion of the smallest cross section and the filament tapers continuously at least section-wise towards the portion of the smallest cross section. Due to a tensile stress in the meander pattern, the deformation of the arcs of curvature sets in almost simultaneously at the respective portions of the same cross section and then continues in the other portions of the arcs of curvature. It is particularly prevented by the continuous tapering of the arcs of curvature towards the portion of the smallest cross section that the stretching movement of the meander pattern first of all leads to a stretching of individual arcs of curvature. The reason for this is that prior to a complete stretching of an arc of curvature the deformation of an adjoining arc of curvature at the portion of the smallest cross section sets in. This enables a regular expansion of the support prosthesis.

Moreover, a portion of the smallest cross section of an arc of curvature may be arranged aside a centerline of the arc of curvature. The portion of the smallest cross section can be located in the area of the apex of the arc of curvature.

For reasons of completeness it must be mentioned that when using a plurality of adjacently arranged support rings, the two outer support rings may have at least outwardly directed arcs of curvature, which are made regular again so that the apices of these arcs of curvature are located in one plane and none of the arcs of curvature projects towards the outside.

The invention will now be described in detail by means of the drawings.

By means of FIG. 1, the fundamental structure will now be explained by means of a schematic view. For reasons of simplification fine structures are shown over the full area and the individual meander shapes or filaments cannot be recognized.

Figure 1:
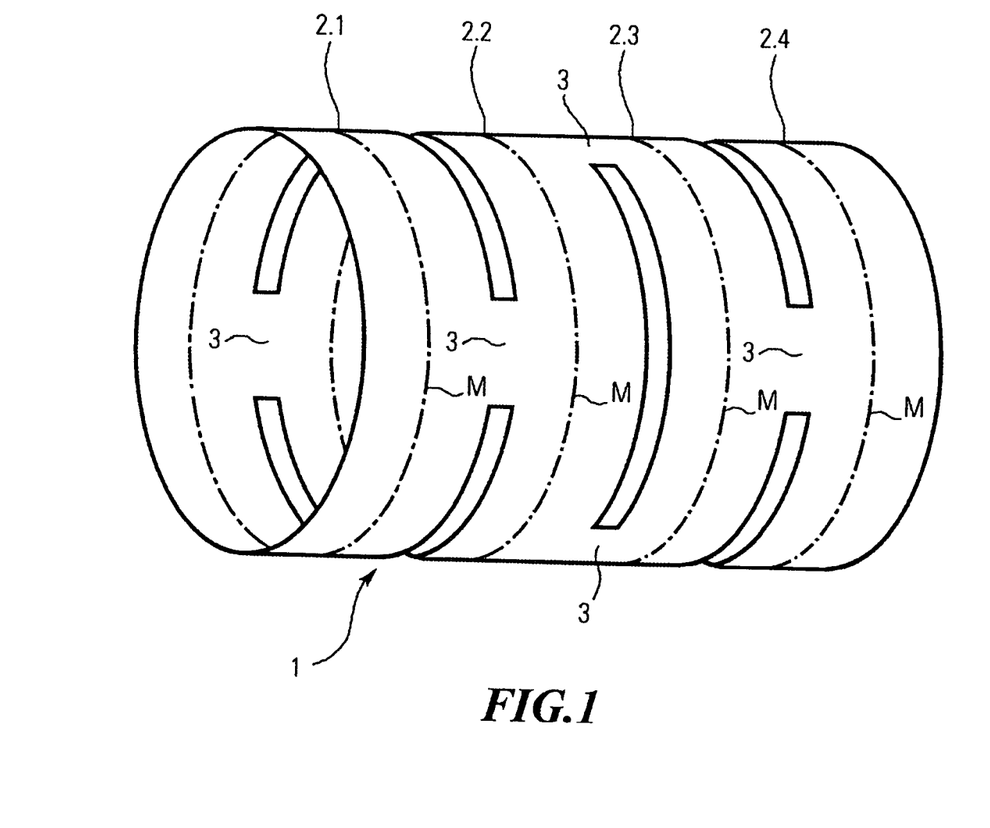
FIG. 1 shows a schematic view of a support prosthesis having four support rings.

The support prosthesis 1 shown in FIG. 1 comprises four adjacently arranged support rings 2.1, 2.2, 2.3 and 2.4, which are connected to one another via joints 3 arranged between the support rings 2.1-2.4. In the present example the two joints are arranged between the individual support rings 2.1-2.4.

The support prosthesis is expandable by means of a balloon catheter from the position that is shown in FIG. 1 into an expanded position. For this purpose, each support ring 2.1-2.4 has a filament not shown in FIG. 1, which circulates in a meander-like manner. This meander shape confers on each support ring 2.1-2.4 the respective expansion properties. The joints 3 are, as will be described in detail below, formed by overlappings of arcs of curvature of adjoining support rings 2.1-2.4. In FIG. 1 the circumferential centerlines M of the support rings 2.1-2.4 are also drawn-in.

By means of FIG. 2 to 4 schematic developments of the meander shape of the support prosthesis schematically shown in FIG. 1 will be explained in detail. As in FIG. 1, four support rings 2.1-2.4 (in the development shown as flat bands) are arranged in juxtaposition in FIG. 2. The development shows the entire circumference of the support prosthesis.

Figure 2:
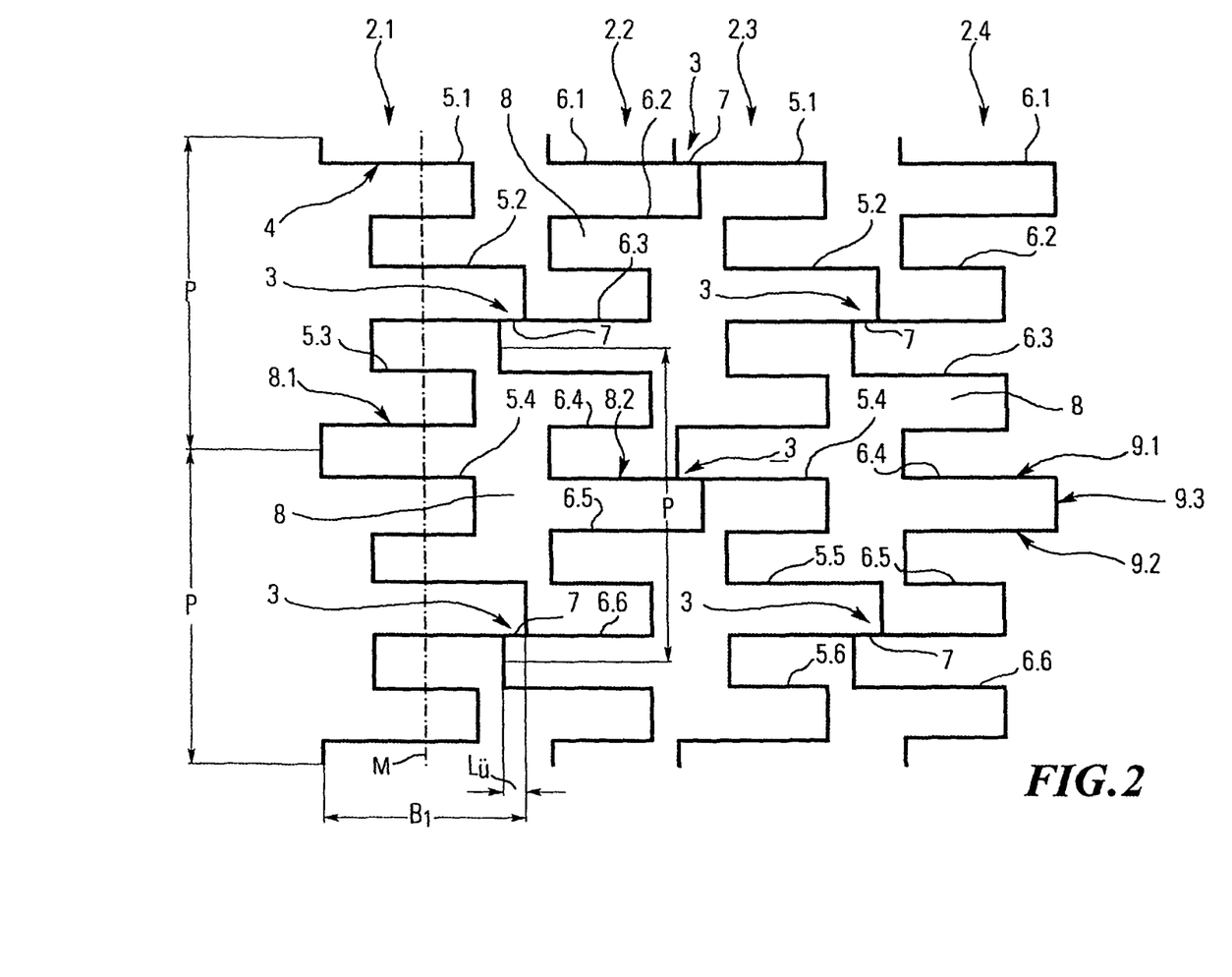
FIG. 2 shows a schematic view of a development of a first embodiment of a support prosthesis.

Each support ring 2.1-2.4 consists of a meander-shaped circumferential filament 4, which is shown in FIG. 2 as a line for reasons of simplification, in the concrete application, however, a three-dimensional thin and narrow band is shown. In the present example the support ring 2.1 has six arcs of curvature 5.1-5.6 directed in the direction towards the second support ring 2.2. While the arcs of curvature 5.1, 5.3, 5.4 and 5.6 end on the same level, the arcs of curvature 5.2 and 5.5 project thereover. The support ring 2.2 has six arcs of curvature 6.1-6.6 directed in the direction towards the first support ring 2.1. While the arcs of curvature 6.1, 6.2, 6.4 and 6.5 end on the same level and at a spacing to the first support ring 2.1, the arcs of curvature 6.3 and 6.6 project on this side and overlap the associated arcs of curvature 5.2 and 5.5 of the first support ring 2.1. The overlapping takes place in a manner that a connection in the overlapping portion takes place at the same time so that the joint 3 is formed. A small filament section 7 is commonly associated to both arcs of curvature 5.2 and 6.3, or 5.5 and 6.6, respectively. The cross section of the common filament section 7 is not substantially changed compared to the rest of the cross section of the arc of curvature to avoid material accumulations as far as possible.

The width $B_1$ of the support ring 2.1 is in the present case approx. 2.5 mm and the length $L_{\ddot{U}}$ of the overlapping portion or common filament section 7 is 0.3125 mm. Thus, the ratio V between $L_{\ddot{u}}$ and $B_1$ is in the present case 0.125.

The arcs of curvature 5.1, 5.2 and 5.3 form a periodically recurring pattern with the period P. In the present case this pattern appears twice on the circumference of the support prosthesis 1 so that the arcs of curvature 5.4, 5.5 and 5.6 have the same meander form and size. The support ring 2.2 is designed substantially identical to the support ring 2.1, however, it is arranged in a phase-shifted manner. The support ring 2.3 is arranged in phase with the support ring 2.1 and is formed identically. The support ring 2.4 is designed in phase and identical to the support ring 2.2.

A prosthesis window 8 is formed between the two joints 3 of the support rings 2.1 and 2.2, said window having a frame half 8.1 substantially formed by the first support ring 2.1 and a frame half 8.2 substantially formed by the second support ring 2.2. The frame halves 8.1 and 8.2 are designed in a centrical manner with respect to each other. Two of these prosthesis windows 8 each are arranged between the first and the second support ring 2.1 and 2.2. The same applies for the respective prosthesis windows 8 between the second and the third support ring 2.2 and 2.3 and the third and fourth support ring 2.3 and 2.4.

It is described by way of example by means of the support ring 2.4 that each arc of curvature comprises a first leg 9.1, a second leg 9.2 and an apex portion 9.3 connecting same with one another. In the present example all arcs of curvature have an identical width, and the legs 9.1 and 9.2 extend substantially axially parallel with respect to a prosthesis main axis A. Thus, the common filament section 7 also extends substantially axially parallel. For reasons of simplification, the apex portion 9.3 is shown in a straight manner in the present example; however, this apex portion is usually formed by a transitional arc. It can well be seen from FIG. 2 that in the present example all arcs of curvature have the same width. Since FIG. 2 is a schematic view, by means of which the fundamental principle is to be explained, it can well be understood that in practical application there are usually no sharp transitions between individual arc of curvature sections but that transitions in the form of radii or arc sections are used. If the structure shown in FIG. 2 is wound to a tubular shape or worked out of a tube, this structure may be expanded during following steps. Since the common filament sections 7 have a slightly different deformation behavior than the rest of the arcs of curvature, they pivot during expansion in a manner that the support rings 2.1-2.4 are pushed apart in the axial direction while same enlarge in circumference. Thus, the length is substantially maintained. A maximum change in length of 5% is desired.

A further embodiment will now be explained in detail by means of FIG. 3. Only the essential differences will now be explained. If elements identical in construction or function are used, the same reference numerals are used. Otherwise, reference is made to the above description.

The main difference is that the meander shape has three different shapes of arc of curvature within one period. The arcs of curvature 5.1, 5.2 and 5.3 each have a different width, so that a somewhat more irregular structure results. All other above described parameters remain substantially equal. For instance the prosthesis windows 8 are formed centrically with respect to their two frame halves 8.1 and 8.2, the support rings 2.1 and 2.3 are formed in phase and identical, the support rings 2.2 and 2.4 are formed in phase and identical etc.

Figure 4:
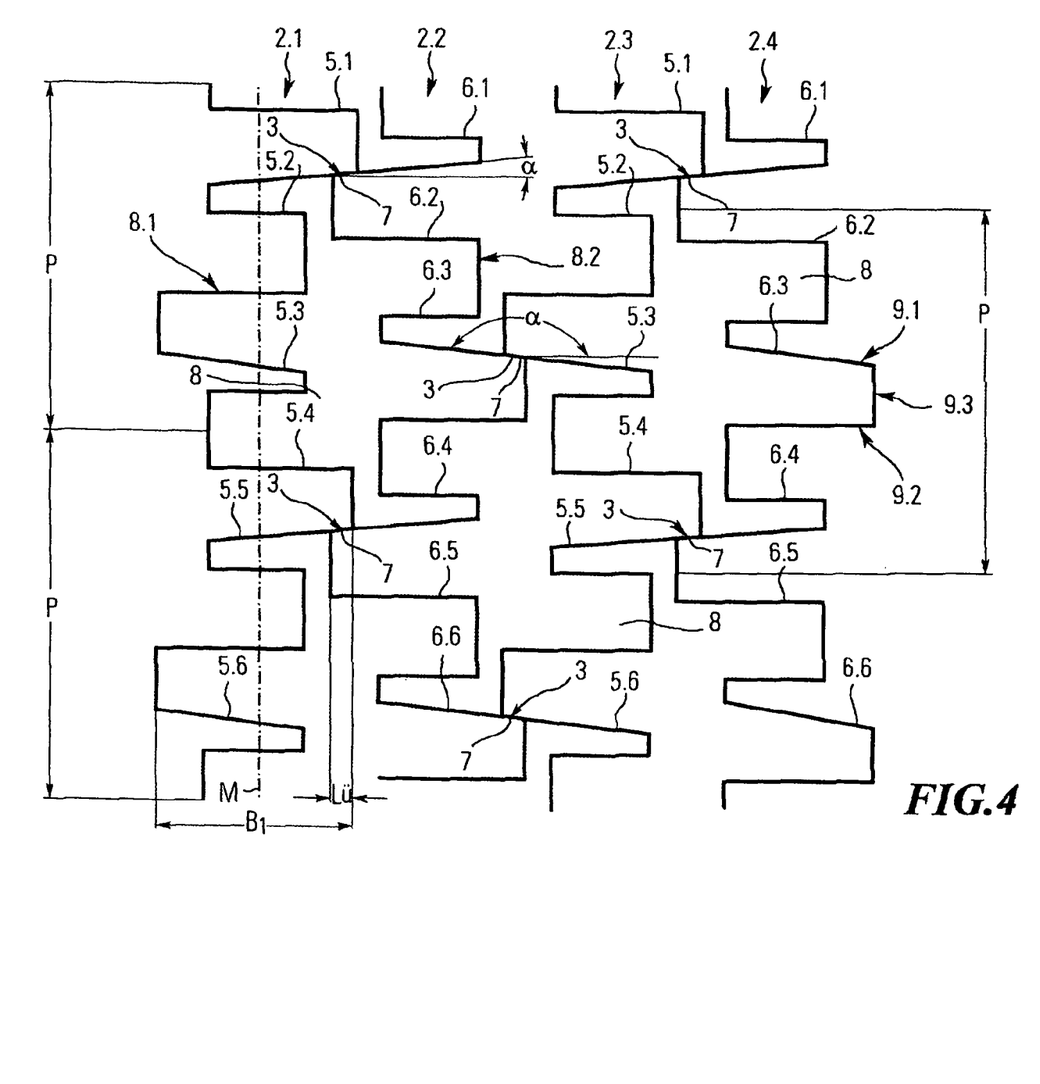
FIG. 4 shows a schematic view of a development of a third embodiment of a support prosthesis.

Regarding the embodiment according to FIG. 4, only the essential differences to the preceding embodiments are explained. Thus, identical reference numerals are used for identical components having an identical function and reference is made to the above description.

Figure 3:
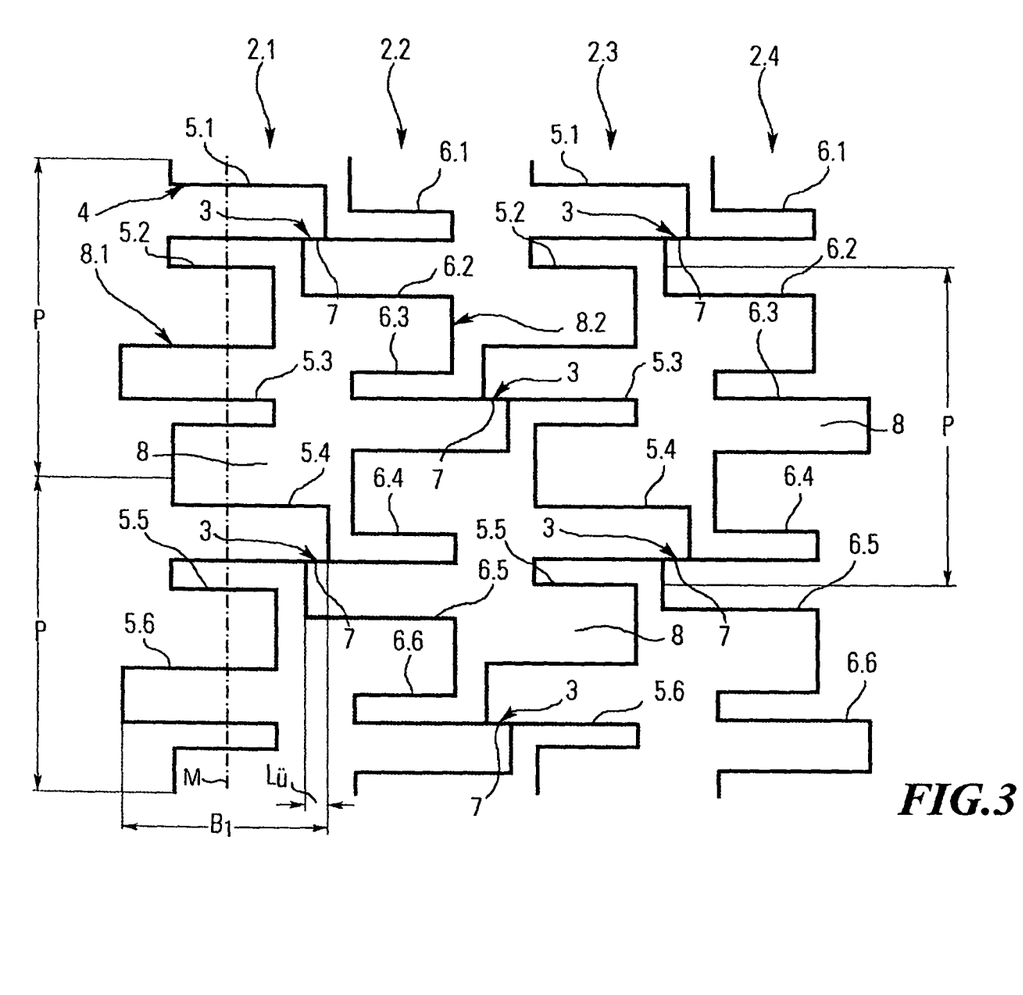
FIG. 3 shows a schematic view of a development of a second embodiment of a support prosthesis.

Contrary to the embodiment of FIG. 3, obliquely extending legs 9.1 and 9.2 of some arcs of curvature (e.g. 5.1 and 6.2) are provided in addition to the different widths of the three arcs of curvature 5.1, 5.2 and 5.3 in one phase. By this the common filament section 7 in the transitional area is oriented obliquely at an angle α, which in the present example is approx. 5° between the first and the second support ring 2.1 and 2.2, and which is approx. 175° between the support rings 2.2 and 2.3. It is measured relative to a reference line, which is a parallel with respect to the prosthesis main axis A. The orientation of the common filament sections 7 between the first and the second support ring 2.1 and 2.2 is opposite to the orientation of the common filament sections 7 between the second support ring 2.2 and the third support ring 2.3. Further, as in the preceding embodiments, the joints 3 are arranged between the second support ring 2.2 and the third support ring 2.3 between the joints 3 of the first support ring 2.1 and the second support ring 2.2. Caused by this embodiment, the common filament sections 7 pivot in the opposite direction when expanding the support prosthesis 1. Moreover, these sections can be pivoted more easily than the axially parallel orientation according to FIGS. 2 and 3. By this a further regularity is achieved. Also caused by the different widths of the arcs of curvature, a dosed, possibly also step-wise expansion results.

Figure 5:
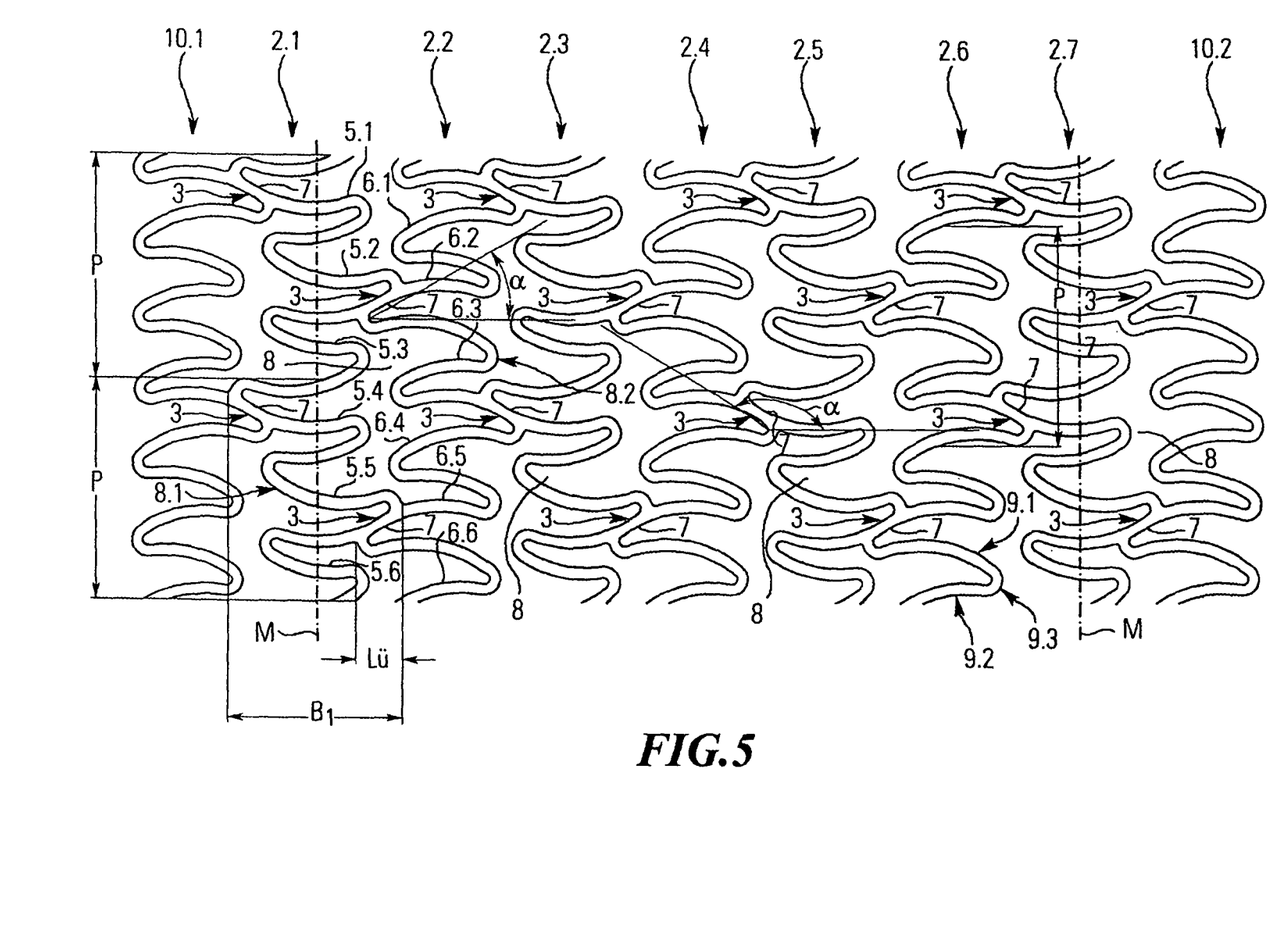
FIG. 5 shows a true to scale view of a development of a fourth embodiment of a support prosthesis.

By means of FIG. 5 the currently favored embodiment is explained in more detail. Reference is also made in this case as far as possible to the above description and the same reference numerals are used for identical components and components having an identical function.

In order to form the ends of the support prosthesis 1 as regular as possible, an end support ring 10.1 and 10.2 is provided at each end. In these end support rings, all arcs of curvature that project towards the front end end on the same height. In this respect, the end support ring 10.1 does not fulfill all symmetry criteria as in the preceding examples. On the whole seven support rings 2.1-2.7 exist. The end support ring 10.2 also does not fulfill all symmetry criteria with respect to the last support ring 2.7. The support rings 2.1, 2.3, 2.5 and 2.7 are designed in phase and identically. The same applies to the support rings 2.2, 2.4 and 2.6, which are also designed in phase and identical with respect to one another. Both the legs 9.1 and 9.2 as well as the apex portions 9.3 are curved in the present example. In the support ring 2.1 the curvature of the legs 9.1 and 9.3 is implemented in that the convex sides in FIG. 5 point downwards and the concave sides point upwards. Thus, all arcs of curvature 5.1-5.6 are curved in the same direction and their contour substantially has a claw or fin shape. The ratio V of $L_ü$ and B1 is in the present case 0.265, wherein $B_1$ is approx. 2.54 mm and $L_ü$ is approx. 0.69 mm.

The second support ring 2.2 is designed such that the legs 9.1 and 9.2 of the arcs of curvature 6.1-6.6 with their convex side 5 point upwards and point downwards with their concave side and are therefore curved opposite to the arcs of curvature 5.1-5.6 of the support ring 2.1. This again leads to a centricality of the prosthesis windows 8. On the whole, three different arcs of curvature (e.g. 5.1, 5.2 and 5.3) exist in each one of the support rings 2.1-2.7.

The angle α between the support rings 2.1 and 2.2 as well as 2.3 and 2.4, 2.5 and 2.6 is 25° and between the support rings 2.2 and 2.3 as well as 2.4 and 2.5 and 2.6 and 2.7 it is 155°. The joints 3 between the first support ring 2.1 and the end support ring 10.1 as well as the last support ring 2.7 and the end support ring 10.2 are designed in an identical manner.

When expanding the support prosthesis 1, the common filament sections 7 between the first and the second support ring 2.1 and 2.2 pivot in a counterclockwise direction, and between the support rings 2.2 and 2.3 they pivot in a clockwise direction. The same applies to the joints 3 between the respective other support rings depending on the orientation of the common filament sections 7. The change in length during expansion is therefore a maximum of 2 to 3%. For this the joints 3 are responsible due to their orientation and design. Moreover, the bent or re-curved arcs of curvature (5.1-5.6, 6.1-6.6) are responsible for the fact that an even smaller inclination for erecting the arcs of curvature (5.1-5.6, 6.1-6.6) exists during expansion. Moreover, the shape of the prosthesis windows 8 leads to the fact that these windows do not expand too broadly during expansion and therefore have a regular expansion behavior. In the initial diameter of the support prosthesis 1 of 2 mm the surface of one prosthesis window 8 is approx. 4.89 mm². During the subsequent expansion to a diameter of 4 mm the surface is approx. 11.26 mm², which corresponds to an enlargement factor of 2.3. Such tubular support prostheses 1 are crimped onto a balloon catheter before implantation, which leads to another diameter reduction, e.g. to 1 mm. The surface of the prosthesis windows 8 is then only 2.81 mm², which corresponds to a reduction to almost half.

An embodiment in the fine structure of the arcs of curvature will now be explained by means of FIG. 6 to 9. Such measures in the fine structure may also be applied in all preceding embodiments. The symmetry criteria mentioned with respect to the above-mentioned embodiments shall also be understood independent of (i.e. with or without) such possibly existing additional measures and are possibly not taken into consideration in the evaluation of symmetry.

Figure 6:
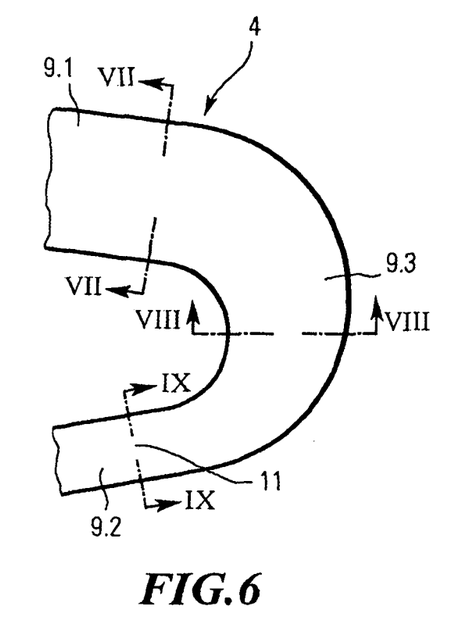
FIG. 6 shows an enlarged view of an apex portion of an arc of curvature according to a further variant.
Figure 7:
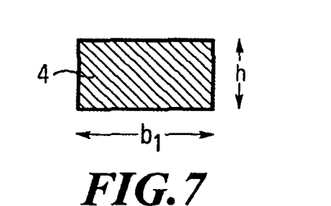
FIG. 7 shows a cross section of the arc of curvature of FIG. 6 along the intersecting line VII-VII.
Figure 8:
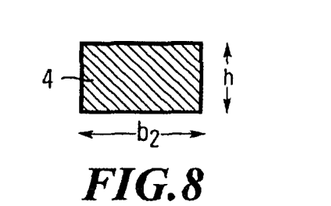
FIG. 8 shows a cross section through the arc of curvature of FIG. 6 along the intersecting line VIII-VIII.
Figure 9:
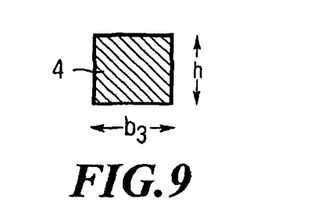
FIG. 9 shows a cross section through the arc of curvature of FIG. 6 along the intersecting line IX-IX.

FIG. 2 shows an enlarged view of an arc of curvature (e.g. 5.1). The arc of curvature has a portion of the smallest diameter 11. While the leg 9.1 and the leg 9.2 both have a constant cross section, the cross section tapers continuously in the area of the apex portion 9.3. It is generated by an outer and an inner radius of curvature, which have a center offset with respect to one another.

Due to the fact that the support prosthesis 1 is made of a metal tube, the support rings 2.1-2.7 as well as 10.1 and 10.2 are fashioned from the metal tube by means of a laser. Thus, the cross sections shown in FIG. 7 to 9 each have the same height h. The cross-sectional surfaces, however, differ in width. The width continuously decreases from $b_1$ to $b_3$.

The type of design of the portion of the smallest cross section 11 as well as the arrangement thereof may deviate from this example. It could also be arranged symmetrically in the center of the apex portion 9.3, wherein the two legs 9.1, 9.2 have the same cross section. This decisively depends on the desired deformation properties, particularly around which point the structure is to bend open. The apex portions 9.3, which adjoin the common filament sections 7 or form a part thereof, may be designed in this manner. The portions of the smallest cross section 11 may also extend across a longer section of the arcs of curvature.

Figure 10:
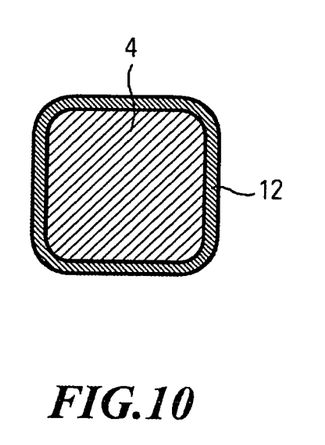
FIG. 10 shows the cross section similar to FIG. 9 in a variant with description.

A further embodiment is shown in FIG. 10 in which a coating 12 is provided. The coating 12 is a silicon dioxide-containing coating, i.e. a glass-like coating. The carrier material is preferably a metal alloy, particularly a steel alloy, on which this coating 12 is applied. Such a coating 12 shall particularly prevent uncontrolled depositions such as plaque, etc. Especially due to the glass-like surface with silicon dioxide a covering of the cells of the body or an adherence of such cells is substantially prevented, which due to its hardness counteracts a damage when attaching the support prosthesis 1 into the body and thus facilitates handling. Due to the thinness of the coating a simple design of the support prosthesis 1 is allowed. Moreover, this prosthesis has a reduced friction caused by lower roughness values and thus a lower load for blood components and a lower coagel formation. Even after a longer dwelling time in the body is there no degradation of the coating. In cooperation with the design of the support ring according to the invention it is ensured that during the expansion process the coating 12 is not damaged or particularly blisters at some portions. Due to the structure chosen, torsional forces during the expansion process are particularly kept low. It can well be seen in FIG. 10 that the edges of the filament 4 are rounded by means of electro-polishing.

The invention claimed is:

1. Tubular support prosthesis for vessels or intercorporeal lumina, comprising at least two expandable support rings adjacently arranged along a support prosthesis main axis and connected to one another at least at one joint, said support rings being formed by a filament wound in a meander-like shape to form several arcs of curvature characterized in that each arc of curvature comprises a first lateral side portion, a second lateral side portion and an apex section extending between these side portions, wherein the lateral side portion of at least one arc of curvature of a first support ring and the lateral side portion of one arc of curvature of an adjacent second support ring laterally overlap and the joint is formed in the overlapping portion; wherein the overlapping arcs of curvature in the overlapping portion comprise common filament sections which form the joint, with an adjoining support ring and on the other side with a further adjoining support ring, and wherein the meander-like shape of the filament of a support ring comprises at least two different arc of curvature shapes or sizes, which commonly form a recurrent pattern of the meander-like shape.

2. Support prosthesis as claimed in claim 1, characterized in that a circumferential annular centerline of a support ring is substantially arranged in a cross-sectional plane extending perpendicular with respect to the support prosthesis main axis.

3. Support prosthesis as claimed in claim 1, characterized in that a prosthesis window formed between two overlapping portions connected to one another comprises a first frame half formed by the first support ring and a second frame half formed by the adjacent second support ring, wherein both frame halves are designed in a manner centrical with respect to one another.

4. Support prosthesis as claimed in claim 1, characterized in that the common filament section in the overlapping portions is inclined at an angle larger than 0° relative to a parallel to the support prosthesis main axis.

5. Support prosthesis as claimed in claim 4, characterized in that the angle is 20 to 30° at least at one overlapping portion and 150° to 160° at another overlapping portion.

6. Support prosthesis as claimed in claim 1, characterized in that at least two expandable support rings adjacently arranged are connected to one another by more than one overlapping portion, wherein the common filament sections of the overlapping portion of one support ring is inclined in the same direction as the common filament section of the overlapping portion of the adjoining support rings.

7. Support prosthesis as claimed in claim 1, characterized in that the common filament section of the overlapping portion is inclined on the one side of the support ring in the opposite direction with respect to the overlapping portions on the other side of the same support ring.

8. Support prosthesis as claimed in claim 1, characterized in that the ratio of length of the overlapping portion, seen in the longitudinal direction of the support prosthesis axis, to the width of the support ring is larger than 0.1.

9. Support prosthesis as claimed in claim 1, characterized in the first and second lateral side portions of the arcs of curvature are curved in the same direction.

10. Support prosthesis as claimed in claim 9, characterized in that the first and second lateral side portions of the arcs of curvature of a support ring are curved in the same direction and the first and second lateral side portions legs of the arcs of curvature of the adjoining support rings are curved in the opposite direction.

11. Support prosthesis as claimed in claim 1, characterized in that a coating is provided on the filament, said coating comprising silicon dioxide.

12. Support prosthesis as claimed in claim 1, characterized in that each arc of curvature comprises a portion of the smallest cross section of the filament and the filament continuously tapers at least section-wise towards the portion of the smallest cross section of the filament.

13. A tubular support prosthesis for vessels or intercorporeal lumina, comprising:
- at least two expandable support rings adjacently arranged long a support prosthesis main axis and connected to one another at least at one joint wherein a support ring is circumferentially alternately connected on the one side with an adjoining support ring (2.2) and on the other side with a further adjoining support ring, said support rings being formed by a filament wound in a meander-like shape to form several arcs of curvature comprising a first lateral side portion, a second lateral side portion and an apex section extending between these side portions;
- a first overlapping portion formed by the lateral side portion of at least one arc of curvature on one side of a first support ring and a lateral side portion of one arc of curvature on one side of an adjacent second support ring laterally overlapping each other;
- a second overlapping portion formed by the lateral side portion of at least one arc of curvature on the other side of said first support ring and the lateral side portion of one arc of curvature of an adjacent third support ring laterally overlapping each other, each of said overlapping portions comprising a common filament section which forms said at least one joint; and said common filament sections being inclined at an angle relative to a parallel to the support prosthesis main axis, wherein said common filament section of said first overlapping portion is inclined in the opposite direction with respect to said common filament section of said second overlapping portion; and wherein the meander shape of the filament of a support ring comprises at least two different arc of curvature shapes or sizes, which commonly form a recurrent pattern of the meander shape.

14. The support prosthesis of claim 13, wherein a circumferential annular centerline of a support ring is substantially arranged in a cross-sectional plane extending perpendicular with respect to the support prosthesis main axis.

15. The support prosthesis of claim 13, wherein a prosthesis window formed between two overlapping portions connected to one another comprises a first frame half formed by the first support ring and a second frame half formed by the adjacent second support ring, wherein both frame halves are designed in a manner centrical with respect to one another.

16. The support prosthesis of claim 13, wherein the angle is 20 to 30° at least one overlapping portion and 150 to 160° at another overlapping portion.

* * * * *